(12) United States Patent
Toh et al.

(10) Patent No.: US 6,242,756 B1
(45) Date of Patent: Jun. 5, 2001

(54) CROSS OPTICAL AXIS INSPECTION SYSTEM FOR INTEGRATED CIRCUITS

(75) Inventors: Peng Seng Toh, Parc Oasis; Chiat Pin Tay, Singapore; Aik Koon Loh, Choa Chu Kang Central; Ying Jian Wang, Singapore, all of (SG)

(73) Assignee: Agilent Technologies, Inc, Palo Alto, CA (US)

( * ) Notice: Subject to any disclaimer, the term of this patent is extended or adjusted under 35 U.S.C. 154(b) by 0 days.

(21) Appl. No.: 09/205,017

(22) Filed: Dec. 4, 1998

(30) Foreign Application Priority Data

May 21, 1998 (SG) .................................................. 9801105.9

(51) Int. Cl.[7] ............................ G01N 21/84; G01B 11/24
(52) U.S. Cl. ...................................... 250/559.34; 356/376
(58) Field of Search ........................ 250/559.34, 559.29, 250/559.31, 559.19, 559.46, 223 R; 356/375, 376, 239.1, 237.4

(56) References Cited

U.S. PATENT DOCUMENTS 6,118,538 * 9/2000 Haugan et al. ................. 250/559.34

* cited by examiner

Primary Examiner—John R. Lee
Assistant Examiner—Kevin Pyo

(57) ABSTRACT

A method and an apparatus for the measurement and inspection of integrated circuit. Such an apparatus includes a camera for sensing an image of the integrated circuit (IC), an oblique light source, and a reflector. The camera has an optical axis passing through the IC normal to the plane of the IC. The oblique light source radiates light on the IC obliquely to the plane of the IC such that at least a portion of the oblique light source is positioned on one side of the optical axis. The reflector is positioned on the opposite side of the optical axis relative the portion of the oblique light source for reflecting light that crosses the optical axis from the oblique light source to the camera, such that at least a portion of the IC interposes between the portion of the oblique light source and the reflector. As a result, the shape of that portion of the IC is imaged on the camera by backlighting. The leads on the IC can be inspected in this manner.

17 Claims, 14 Drawing Sheets

CROSS OPTICAL AXIS INSPECTION SYSTEM FOR INTEGRATED CIRCUITS

This invention relates generally to an inspection system using optical means and more specifically to an optical inspection system for inspecting integrated circuits using imaging techniques.

BACKGROUND

The inspection of leads of Integrated Circuit (IC) packages is extremely important to the electronics industry. IC packages such as Quad Flat Pack (QFP), Plastic Leadless Chip Carrier (PLCC), Small Outline IC (SOIC), Small Outline J-Lead (SOJ), Dual-In-Line Pack (DIP), Small Outline Transistor (SOT), and their derivatives have leads protruding out from the IC package body. These leads are the means for electrically connecting the internal circuits to the outside world. The integrity of these leads is crucial for providing good electrical connectivity and therefore useful application of the IC.

An Integrated Circuit (IC) package typically has a square or rectangular plastic package moulded over and encapsulating the IC circuitry commonly known as the "die". The size of the package may range from 4×4 mm square to 32×32 mm square. Extending from the plastic package are leads that provide electrical connectivity between the die inside the IC package and the printed circuit boards (PCBs). It is important for IC packages and their leads to possess accurate and consistent mechanical dimensions because highly automated PCB assembly machines are used to place and solder the ICs onto PCBs. Damaged, twisted, or out-of-place leads will likely lead to improper assembling of the PCB assembly, and hence the malfunction of the PCB assembly. In particular, for high lead count ICs such as the Quad Flat Pack (QFP) which has leads on all four sides of the package, the mechanical requirements are even more stringent. There are several requirements of the leads and categories of defects that have to be measured, the leads requirement including coplanarity, lead pitch, terminal dimension, standoff, and others. Lead defects include bent leads, solder plating defects, swept leads, burr, and the like.

Several techniques and systems that include special optical and lighting arrangements for the direct and indirect viewing of leads of IC packages are available on the market. There are two major categories of IC lead inspection and measurement systems. One category involves the use of laser-scanning techniques. The other category involves the use of shadow casting and backlighting techniques to illuminate the lead profiles onto imaging planes. As an example, one method uses lasers to scan the leads of an IC from the top. Another method uses a backlighting system with an image doubler that increases the resolution of the image. Yet another method uses a lead inspection system to locate the leads with reference to a reference plate on which the device is mounted and a real-time reference which is used to provide a known correlation between the image pixels and linear measurement. One such IC inspection system includes a displacement sensor in which the upward and downward coplanarity error of each lead is measured from a level change in the output signal of the sensor. Another such system determines a position of at least one lead of an electronic component using shadow casting techniques.

The way that the leads are arranged on an IC also determines how the IC will be inspected using the IC inspection systems. This is because ICs with different lead arrangements are transported differently. For example, an IC having leads on all four sides of its package is typically transported by pick-and-place means such as pickup heads. Since these pickup heads move through a range of motion, these IC inspection systems must therefore be designed to not obstruct or impede this range of motion. Whereas in another example, an IC having leads on only two opposing sides of its package is typically transported using a track. Most dual sided ICs such as SOICs, SOJs and DIPs are transported using tracks during electrical testing and visual mechanical inspection. Single sided ICs are also transported for testing and inspection via tracks.

Two types of track feed methods are available. The gravity-feed method uses inclined tracks in which the ICs are loaded from the top of the track at one place and they slide down the track to another place. The force-feed method depends on pushers to push the ICs along a horizontal guided track. Again, the IC inspection systems for dual-sided or single-sided ICs must be adapted to the tracks that transport them.

However, various problems exist with these prior art inspection techniques. In the case of laser scanning technique, the top surface instead of the bottom surface of a lead is measured. This presents a problem because the bottom surface and geometry of a lead is more important than the top surface, particularly in relation to the electrical connectivity of the leads. The thickness of the leads will vary from lead to lead as a result of the solder plating thickness. As a consequence, measuring the top surface of the leads is not as effective to measuring the bottom surface. This is especially true in high precision measurement in the range of several micrometers. In addition, laser-scanning techniques cannot detect burrs on lead tips, which commonly occur as a result of the trim and form process in the manufacture of IC leads. The existence of burrs on lead tips is another important factor that influences the electrical connectivity of an IC package to PCB.

In particular, problems exist in prior art inspection systems for dual-sided ICs transported using tracks. These tracks are typically continuous for the distance that they transport the dual-sided ICs, and thus will impede the imaging of the profiles of the leads in shadow casting and backlighting techniques. Therefore, a prior art solution uses an illuminating track as a backlight. The biggest difficulty encountered in such an implementation is the mounting of the backlight within the track without adversely affecting the speed with which the ICs are transported.

Therefore, there is a need for methods and systems for reliable inspection of ICs, especially for a method and a system that can reliably inspect the bottom surface of the IC leads.

SUMMARY OF THE PRESENT INVENTION

An inspection system for inspecting planar objects (e.g., an IC) that includes a camera for sensing an image of the planar object, an oblique light source, a reflector, and a transparent guide, is provided according to the invention. The camera has an optical axis passing through the planar object normal to the plane of the planar object. The oblique light source radiates light on the planar object obliquely to the plane of the planar object such that at least a portion of the oblique light source is positioned on one side of the optical axis. The reflector is positioned on the opposite side of the optical axis relative the portion of the oblique light source for reflecting light that crosses the optical axis from the oblique light source to the camera. The portion of the light source, the planar object, and the reflector are arranged such that at least a portion of the planar object interposes between the portion of the oblique light source and the reflector. The transparent guide holds the planar object in relation to this arrangement, and thus also interposes between the portion of the oblique light source and the reflector. Therefore, the shape of that portion of the planar object is imaged on the camera by backlighting. During this imaging process, the light that provides the shape propagates through the transparent guide. In this manner, the planar object can be inspected.

The advantages of such an inspection system are manifold. Firstly, planar objects such as ICs may be inspected for lead mechanical dimensions accurately and repeatedly. Secondly, the inspection system is easily adapted to inspect dual-sided ICs where the transparent guide may be used as part of a track that transports the dual-sided ICs. Hence, high throughput without affecting the production rate may be achieved. Finally, the transparent guide may interchangeably work with different tracks holding different types of dual-sided ICs, thereby reducing the amount of time to switch dual-sided ICs during inspection. Higher throughput may be further achieved.

BRIEF DESCRIPTION OF THE DRAWINGS

For clarity, preferred embodiments of the invention are described with reference to the following illustrative figures. In the figures, like numerals refer to like features in the several views.

DETAILED DESCRIPTION OF THE PREFERRED EMBODIMENTS

In one embodiment, the inspection system of the present invention provides a technique for inspecting the bottom portion of the side edges of the object. Furthermore, the embodiment enables the inspection of the object while the object is in motion using a real time reference plane. The reference plane is built into the inspection system and is imaged together with the IC under inspection.

Figure 1:
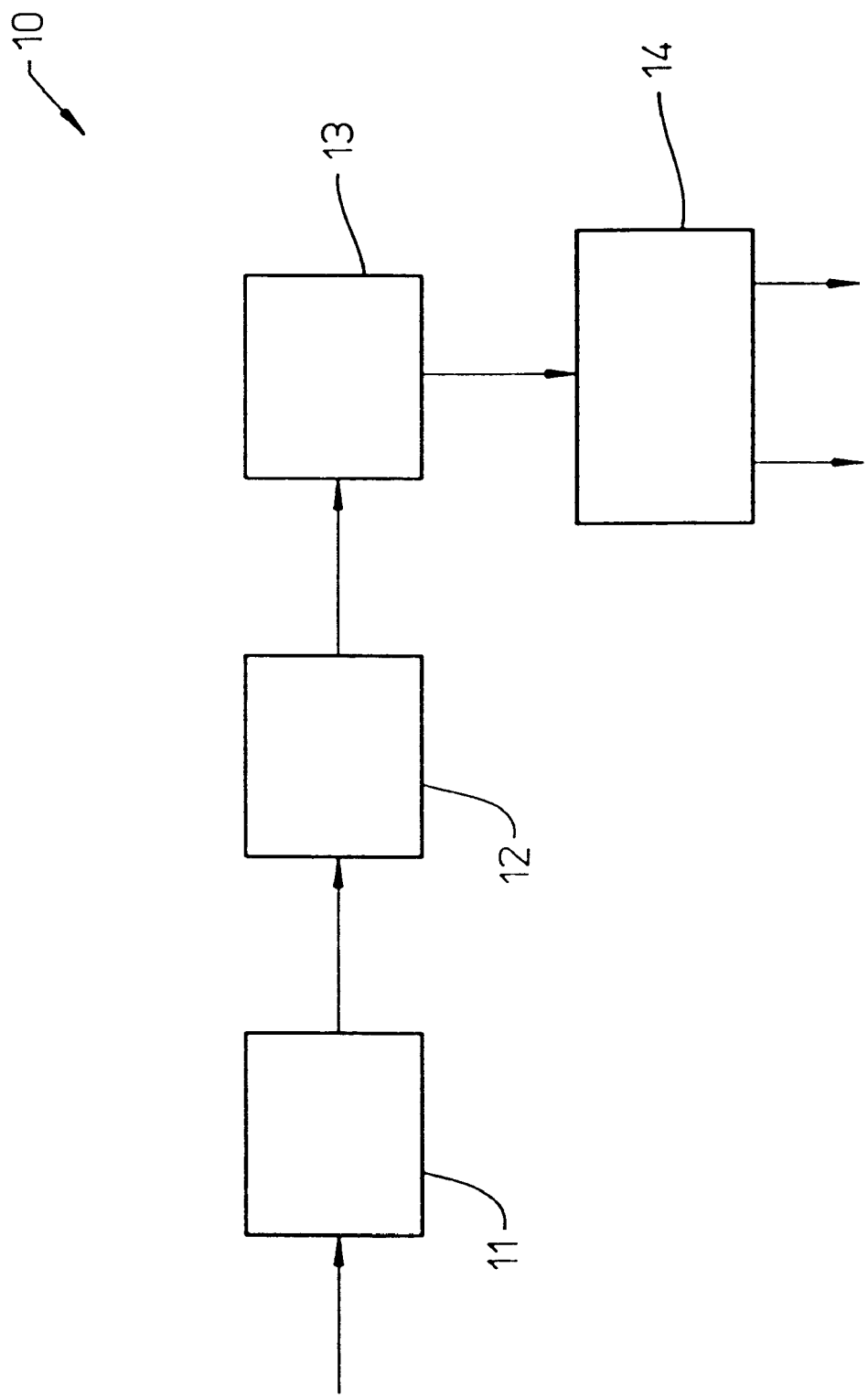
FIG. 1 is a block diagram of an inspection system for integrated circuits (ICs) according to an embodiment of the invention.

FIG. 1 illustrates in block diagram the embodiment of an apparatus for inspecting three-dimensional objects. For convenience and clarity, hereinafter, the description will refer to an embodiment for inspecting three-dimension IC leads, although it is to be understood that the apparatus can be used for inspecting other objects, especially side edges of planar objects. The inspection system 10 includes four modules, namely the viewing optical module 11, the image acquisition module 12, the central processing module 13, and the control module 14.

Figure 2A:
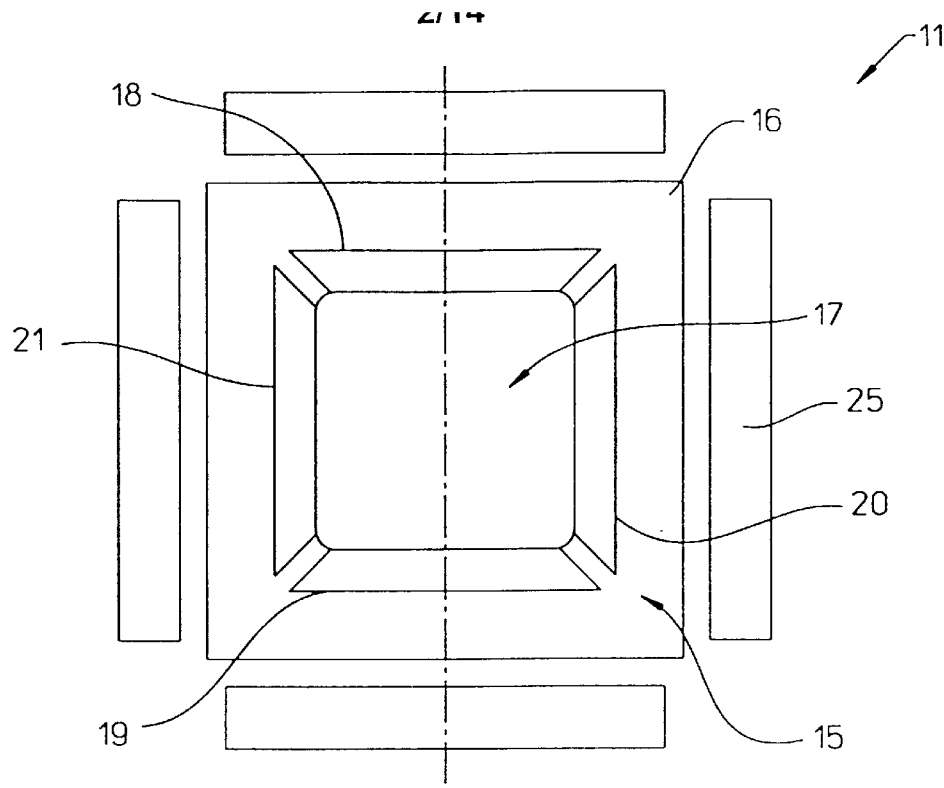
FIGS. 2a and 2b are a plan schematic view and a cross-sectional schematic elevation respectively of a first embodiment of the viewing optical module of the inspection system in FIG. 1.
Figure 2B:
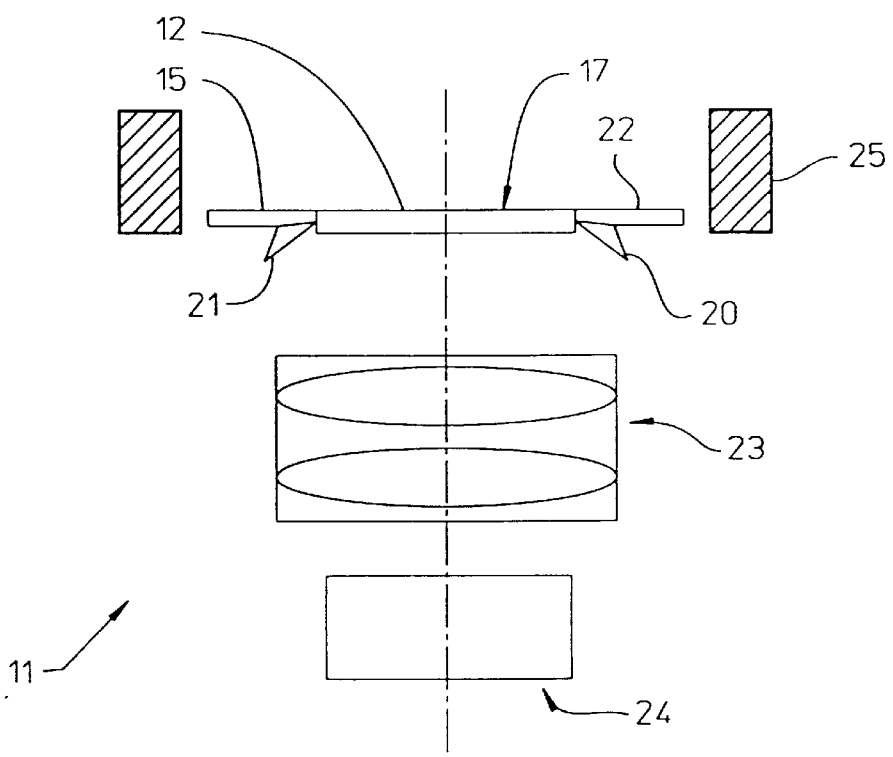

As shown in FIG. 2a, which shows a schematic bottom plan view, and FIG. 2b, which shows a schematic side view, the viewing optical module 11 includes an inspection datum 15 that has a sufficiently flat surface. The inspection datum 15 includes a frame 16 having an opening in its centre. The central opening in the inspection datum 15 is referred to as the viewing window 17. The viewing window 17 is an optically clear aperture allowing light of the desired wavelength to pass through. The size of the viewing window 17 is also adapted to be bigger than the size of the footprint of the IC 100 (not shown in FIG. 2 but shown in FIG. 3 and FIG. 4), which the system is arranged to inspect. The viewing optical module 11 further includes reflectors 18, 19, 20, 21 attached to the frame 16 just below the upper surfaces 22 of the datum 15. These reflectors 18, 19, 20, 21 are generally made up of either mirrors or prisms attached to the frame 16 adjacent the four sides of the viewing window 17.

The viewing optical module 11 of the embodiment shown in FIG. 1 further includes a lens or lens system 23 and video camera 24 and each of the reflectors 18, 19, 20, 21 reflects the light passing through the viewing window 17 into the lens 23 and further into the video camera 24. The lens 23 has telecentric property such that it is sufficiently tolerant to reasonable object distance variations. The video camera 24 is typically a Charged Coupled Device (CCD) camera that has a photo-sensitive array. The field of view of the video camera 24 encompasses the entire viewing window 17 and the four reflectors 18, 19, 20, 21.

The viewing optical module 11 further includes uniformly illuminating light source 25, which have parts that are positioned around the viewing window 17. These uniformly illuminating light source parts 25 are used for backlighting the IC 100. Backlighting is an illumination technique that provides the silhouette of an object on which dimensional measurement can be effectively carried out. In using the backlighting technique, the object (i.e., the IC) to be measured is positioned between the viewer (camera) and the light source.

Figure 3:
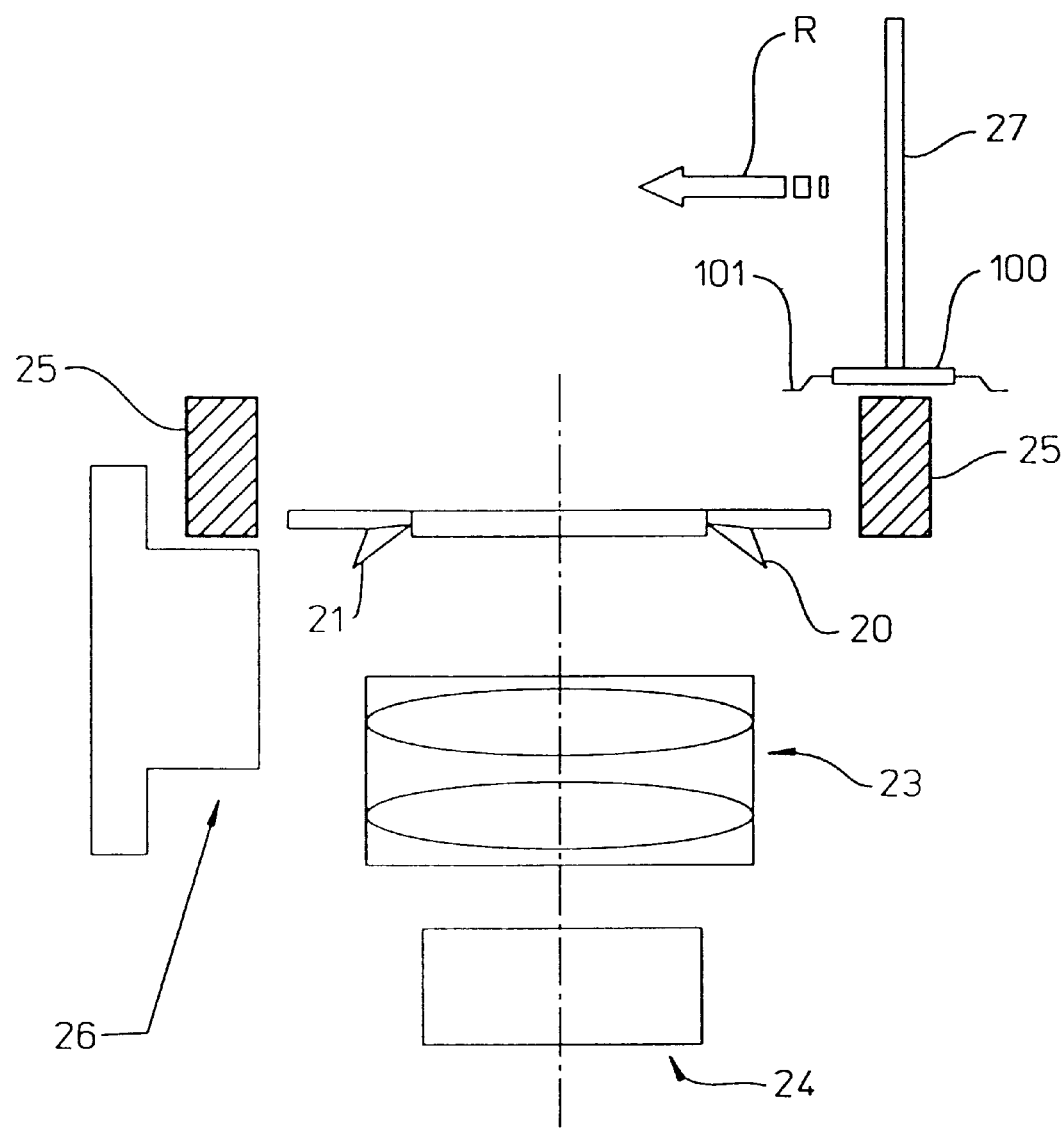
FIG. 3 is a schematic view of the optical module in FIGS. 2a and 2b illustrating the transporting of an IC across the module.

The uniform light source 25 can either be mounted onto the inspection datum 15 or onto a movable platform 26 (as shown in FIG. 3) surrounding the inspection datum 15. When the uniform light source 25 is mounted onto a movable platform 26, it is possible to lower the uniform light source 25 below the inspection datum 15 surface so that the inspection datum 15 is clear of any object that may cause obstruction. In this way, the uniform light source 25 can be moved into place to illuminate the IC 100 for imaging when the IC 100 is proximate to the viewing window 17 (as in FIG. 4). The uniform light source 25 can be moved out of the way to allow the IC 100 to be move into or out of the viewing optical module 11 before and after imaging.

Figure 4A:
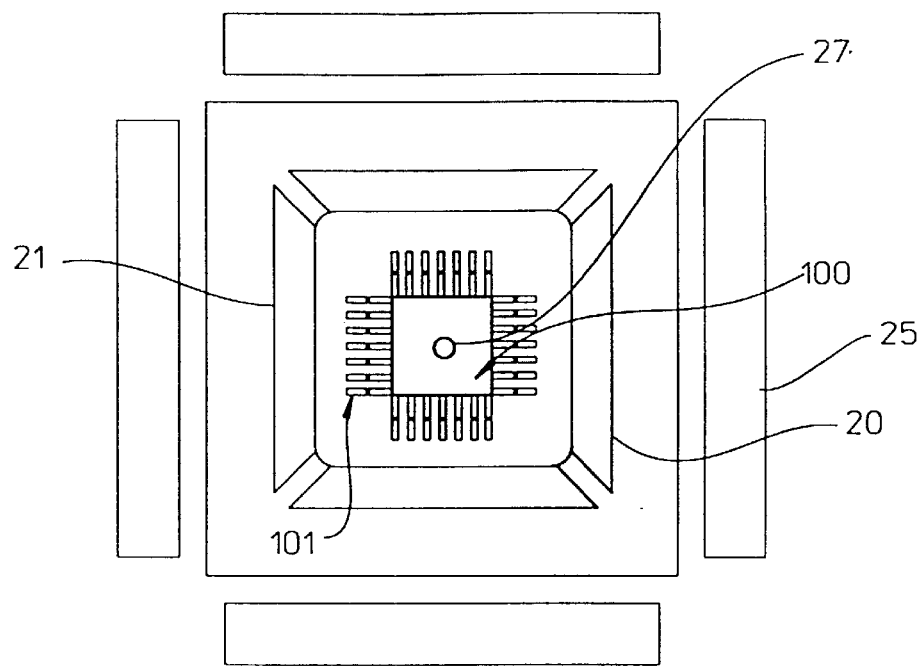
FIGS. 4a and 4b illustrate the viewing optical module with the IC in position.
Figure 4B:
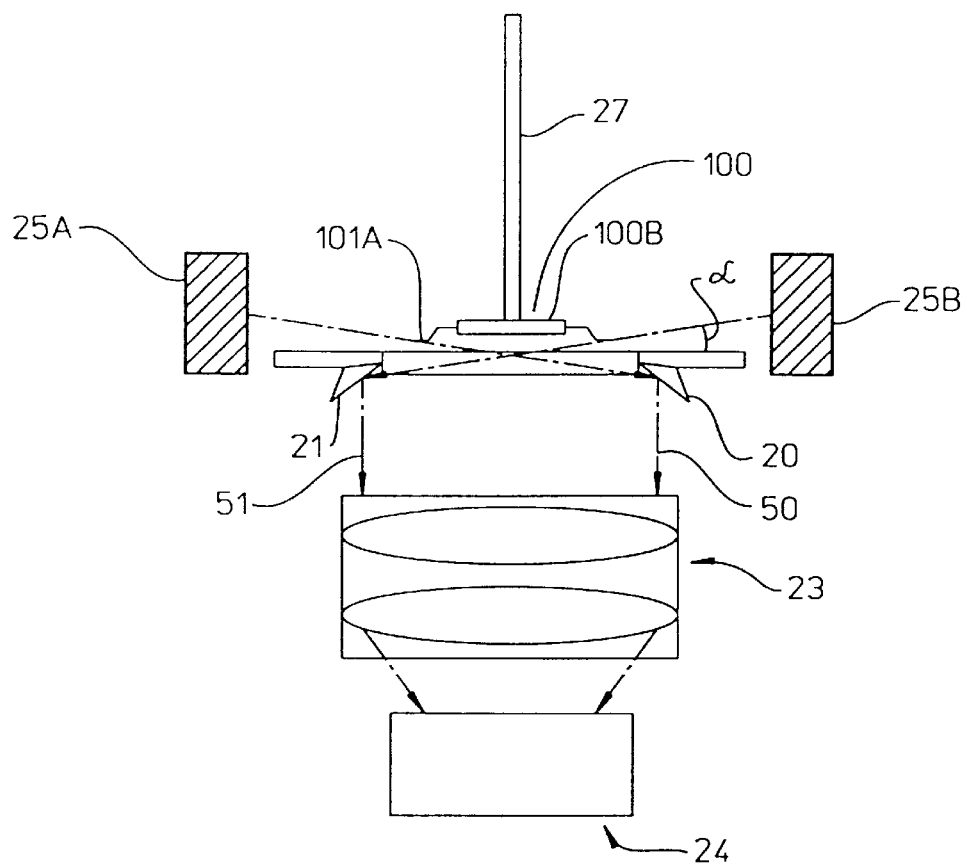

FIG. 3 and FIG. 4 show an example of how an IC 100 can be transported for inspection. As shown in FIGS. 3, 4a and 4b, an IC 100 to be inspected is picked up from the top by means of a pickup head 27 such as a suction cup. Such suction heads and suction cups are known in the art and commonly used in the electronics industry. The pickup head 27 transports the IC over the viewing window 17. The bottom side of the IC 100 remains clear for inspection without any obstruction. The IC 100 is aligned in parallel to the upper surface 22 of the inspection datum 15 with seating plane of the IC 100 largely parallel to this surface 22. A small spacing is maintained between the inspection datum 15 and the seating plane of the IC 100. When the IC 100 is transported across the viewing window 17, no vertical movement is required to lower the IC 100 into the viewing window 17. When the IC 100 is at the appropriate location above the viewing window 17, the uniform light source 25 is moved up by the platform 26 to its active position to provide backlight for the video camera 24 to acquire the image of the IC 100. After the image is acquired, the uniform light source 25 is moved downward to its inactive position to provide a clear passage for the IC 100 to be transported out of its position over the viewing window 17. Alternatively, the light source 25 can be attached to the pickup head 27 and hence move together with the pickup head 27. As best illustrated in FIG. 4b, when the IC 100 is moved to the location of the viewing window 17, the IC 100 is located between the uniformly illuminating light source 25 and the reflector 18, 19, 20, 21. This is a backlighting technique as the reflectors 18, 19, 20, 21 obtain an image of the IC 100 and its leads 101 in silhouette (e.g., see FIG. 8). The video camera 24 hence images the silhouettes of the IC 100 and its leads 101 through the reflector 18, 19, 20, 21 and the lens 23.

It should be noted that each of the reflectors 18, 19, 20, 21 views the leads 101 on the far side (i.e., the side edge remote from the corresponding reflector of the IC 100) hence forming a cross-looking geometry (see FIG. 5). As illustrated in FIGS. 4a and 4b, the reflector 20 reflects the silhouettes, created by light from light source part 25A, of the leads 101A through the optical path 50 into the lens 23 and then into the video camera 24. Similarly, the optical path 51 is a cross looking geometry where reflector 21 reflects light of light source part 25B passing by the leads 101B into the lens 23 and the video camera 24 as a silhouette. If the IC consists of leads 101 on all its four sides, then all the four reflectors 18, 19, 20, 21 will reflect their respective far side leads 101 into the lens 23 and the video camera 24. If the IC 100 consists of leads 101 on only two opposing sides, then only two of the reflectors 18, 19, 20, 21 depending on which orientation the IC 100 is placed above the inspection datum 15 and over the viewing window 17, will reflect their respective far side leads 101 into the lens 23 and the video camera 24. The viewing optical paths have a portion passing by the lead 101 inclining at a small oblique angle α with respect to the inspection datum 15. This oblique angle α further allows leads 101 below the IC 100 package bottom to be successfully imaged and measured. In practice, the oblique angle α is no more than 10 degrees.

Figure 5A:
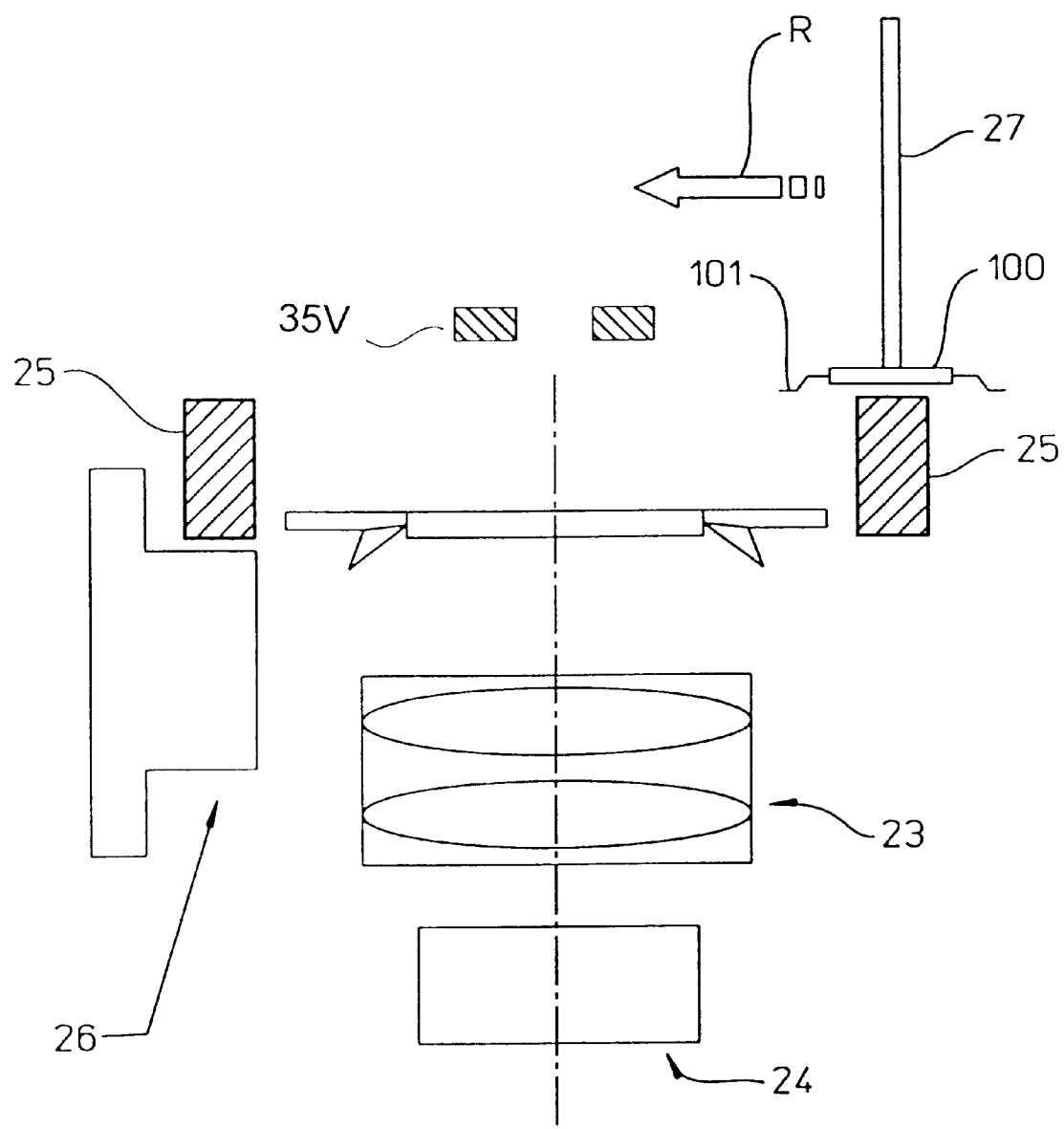
FIG. 5a is a side schematic view of the viewing optical module with a second light source.

As shown in FIG. 5a, a second light source 35V above the IC 100 in addition to light source 25 is used to provide illumination at a substantial angle relative to the light from light source 25. In this case, in a backlighting technique, the IC 100 interposes between the second light source 35V and the video camera 24 such that the light passes the leads 101 of the IC to the camera to form a silhouette type of image (see FIG. 8). Preferably, the light source 35V have portions that can be moved out of the way to allow the IC 100 and the pickup head 27 to pass before and after imaging. Also, if preferred, but not required, the two light sources can be turned on at a different time so that they will not interfere with each other. As used herein, as long as light from the different light sources impinge on the video camera 24 and are sensed simultaneously, such a sensing process by the video camera 24 is considered to be one imaging herein and the image sensed, although having information derived from different light sources, is considered to be a single temporal image.

Figure 5B:
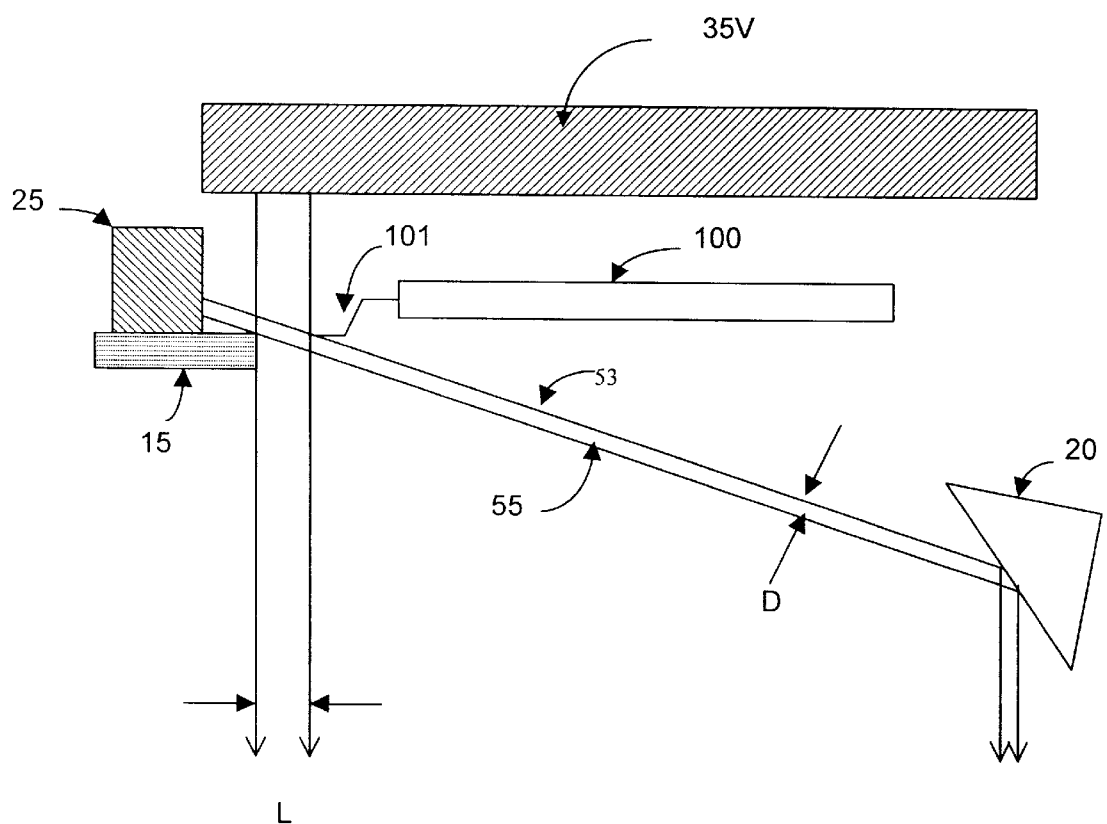
FIG. 5b is a schematic view to an enlarged scale illustrating the imaging of part of the IC.

The technique for using the inspection datum 15 to measure the mechanical dimensions of the leads 101 with respect to the inspection datum 15 is now described. As shown in FIG. 5b, the lead 101 of the IC 100 is imaged by light passing along the optical path 53 and the inspection datum 15 is imaged by light passing along the optical path 55. These two optical paths are reflected by the reflector 20 into the lens 23 and the video camera 24. The perpendicular distance D between these two optical paths can then be determined from the image form at the video camera 24. Note that the light that enables distance D to be measured come from the oblique light source 25. When the top light 35V is used, it backlights the IC 100, its leads 101 and an edge of the inspection datum 15 vertically into the video camera 24. Hence, the horizontal displacement of the lead 101 from the edge of inspection datum 15, which is denoted by L, can be measured from the same image. Using D and L, the three-dimensional, or X, Y, and Z, co-ordinates of the lead 101 with respect to the inspection datum 15 can be determined.

Figure 6:
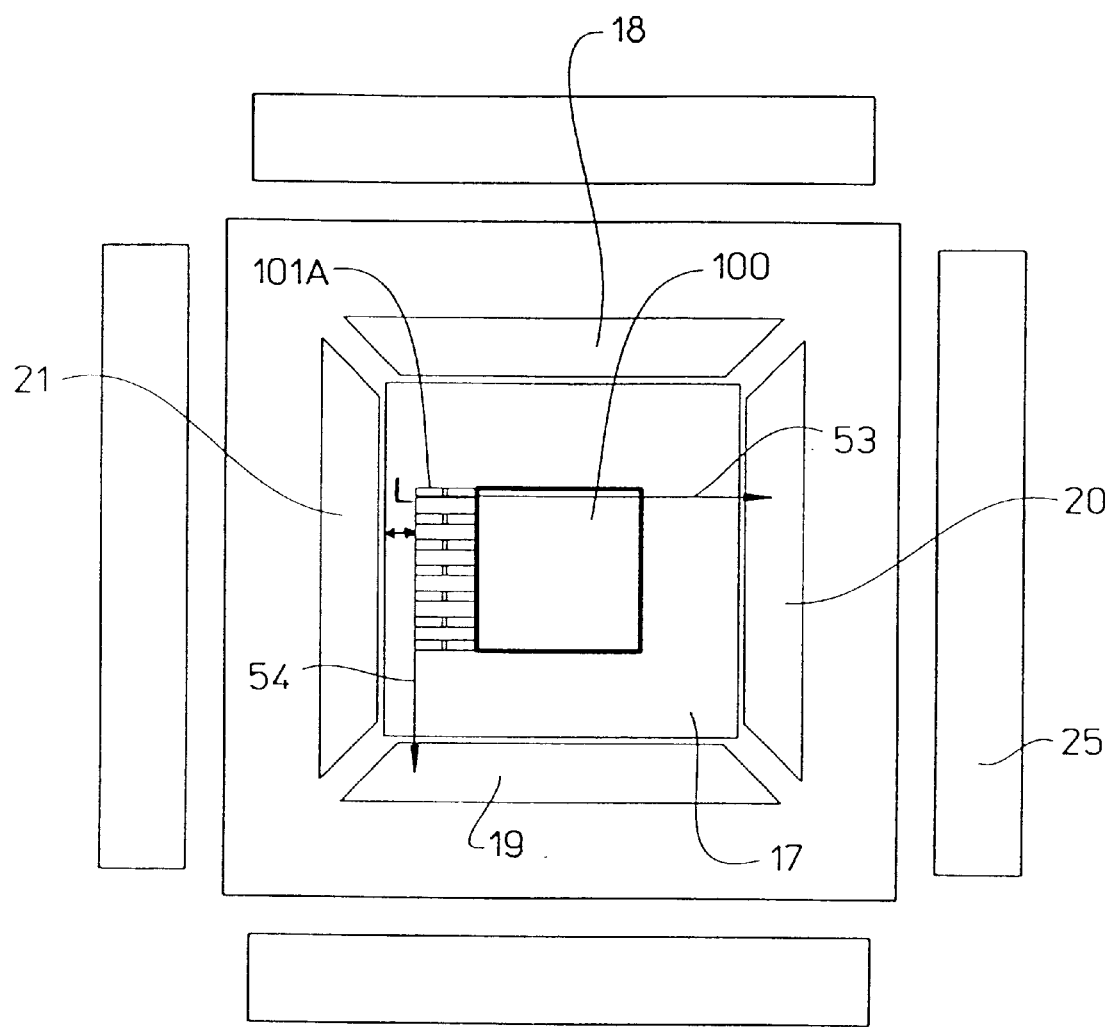
FIG. 6 is a plan view to an enlarged scale of the viewing optical module and IC in position.

FIG. 6 shows a bottom view at the viewing window 17 with an IC 100 at its centre for imaging. Here, for illustrative clarity, leads on only one side edge of the IC 100 are shown. The lead 101A is imaged by light passing along light path 53 onto the reflector 20 and imaged by light passing along light path 54 onto the reflector 19. The light paths 53 and 54 are substantially about 90 degrees to each other. Here, for clarity, the silhouette images reflected by the reflectors 18, 19, 20, 21 are not shown in this figure. The underside of the IC 100 can also be seen if a light is present to illuminate it, for example, as described later relating to FIG. 10.

Figure 7:
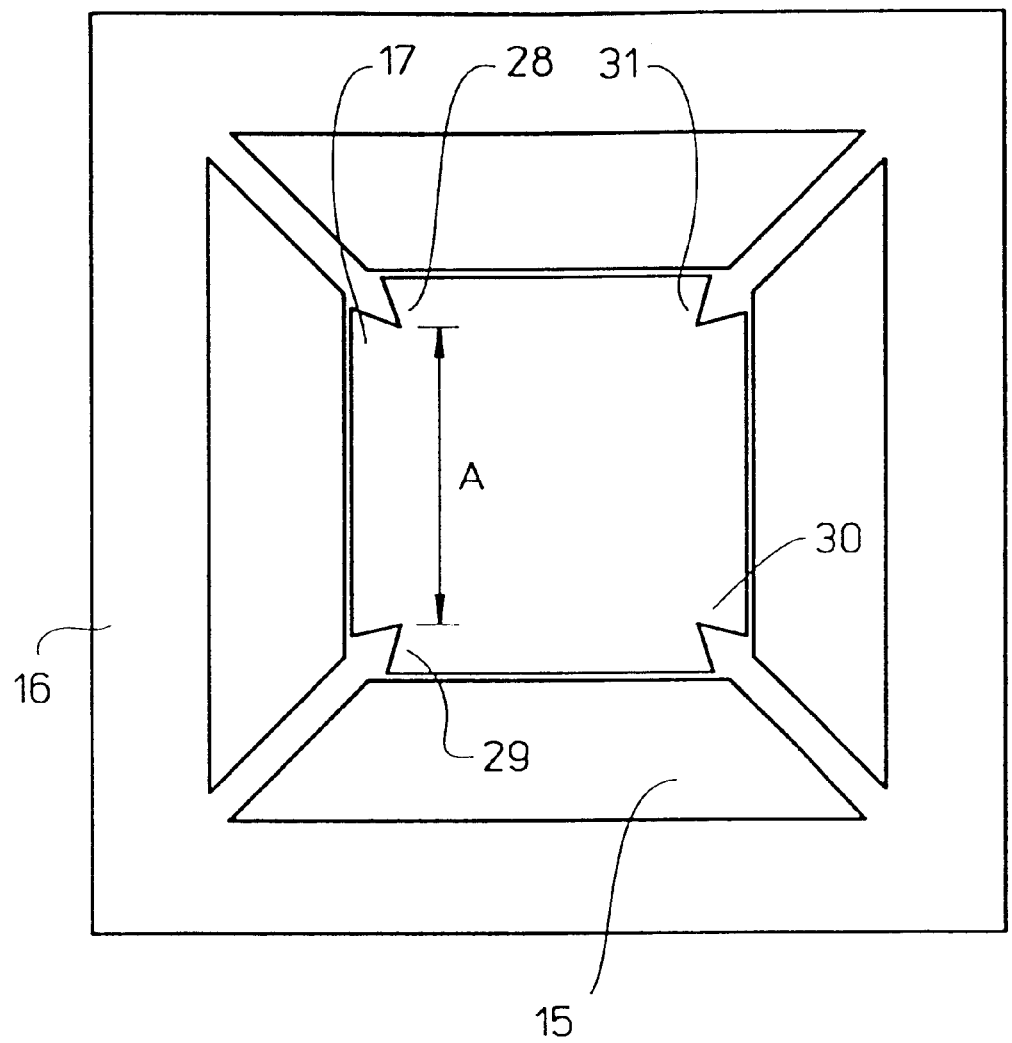
FIG. 7 is a plan view of a variation of the inspection datum of the viewing optical module.
Figure 8:
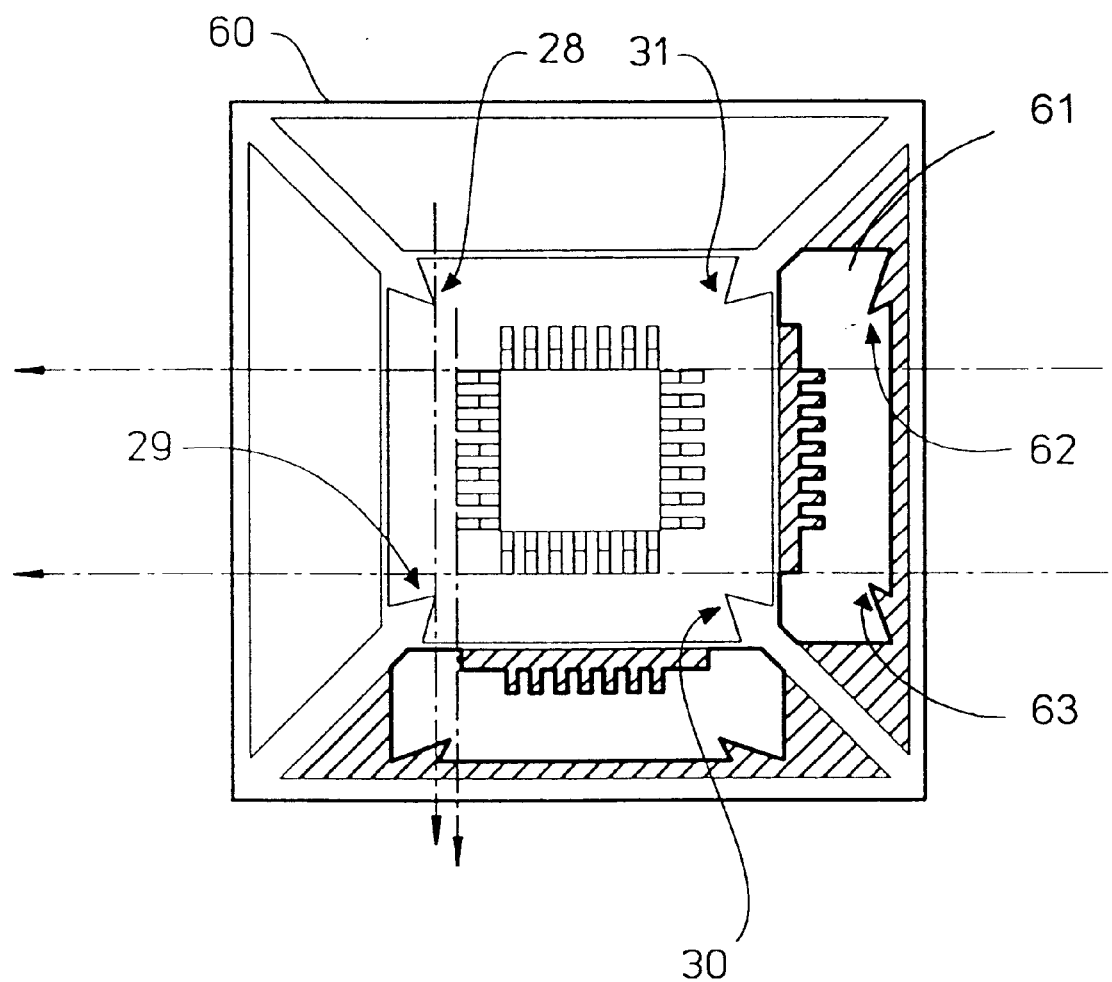
FIG. 8 is a schematic view illustrating the image generated from the viewing optical module.
Figure 9:
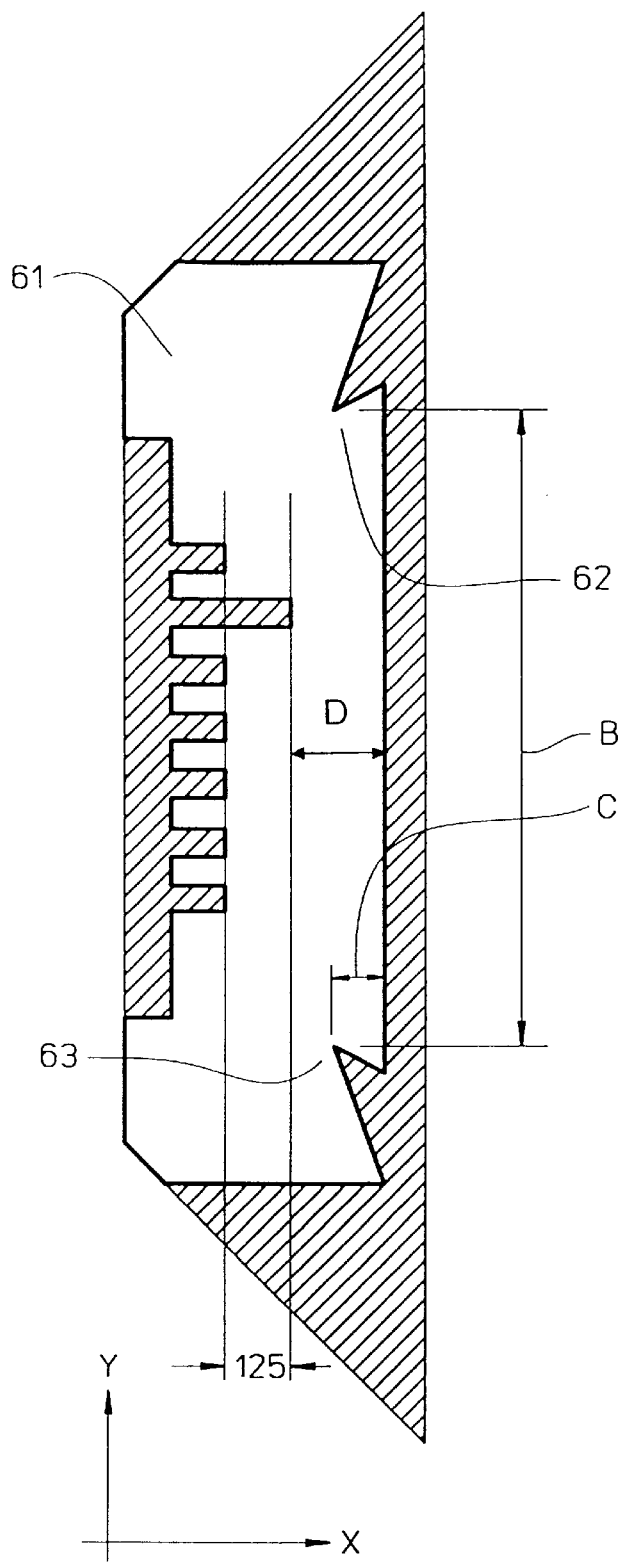
FIG. 9 is a detailed view of a part of the image of FIG. 8.

To facilitate calibration of the inspection system, the frame 16 may include reference points as illustrated in the FIG. 7. In the illustrated form, the dynamic reference points 28, 29, 30, 31 are distributed on the four corners of the viewing window 17. The four dynamic reference points 28, 29, 30, 31 form a known precise reference plane. The distance between any two of these dynamic reference points are precisely known and are pre-stored in the central processing module 13. The dynamic reference points and the inspection datum 15 are preferably machined out from a single piece of rigid material so that high precision and flatness can be maintained. For the purpose of describing the calibration procedure, reference is made to FIGS. 8 and 9. FIG. 8 shows an image 60 acquired by the video camera 24, i.e., as seen from a position under the IC 100, whereas FIG. 9 is a part of this image showing specifically a sub-image 61 reflected from the reflector 20, through the lens 23 and onto the video camera 24. As can be seen, the dynamic reference point 28 is imaged onto point 62, whereas the dynamic point 29 is imaged onto point 63. The physical distance between the two dynamic reference points 28 and 29 is of a known value A (see FIG. 7). As shown in FIG. 9, the distance B between imaged dynamic reference points 62 and 63 is measured in terms of pixels, which is a common term to denote the picture element in an digital array representing an image. Hence it becomes possible to calibrate the Y scale of this part of the sub-image 61, which is reflected by reflector 20. The Y scale is equal to A/B. If A is measured in mm, then the unit for Y scale is mm per pixel. Similarly, the Z scale of this part of the image can be obtained by measuring the distance C, corresponding to how far the dynamic reference 63 extend from the edge of the frame 16, in terms of pixel. The calibration procedure that has been described is equally applicable to all other three reflected sub-images reflected by the reflectors 18, 19, 21. Therefore, using the apparatus of the present invention, one is able to obtain distances in absolute units (e.g., mm, micron) between points in the object in different co-ordinates.

The image acquisition module 12 consists of a frame grabber (not shown in the figures) which receives the video signal from the video camera 24 and converts it into digital format which is known as a digital image corresponding to image 60 (see FIG. 8). It is also common in the art that the video camera 24 may output digital format video signal. The frame grabber further transmits the digital image 60 for digital image processing and analysis to be carried out by the central processing module 13. A sensor may be used to sense the position of the IC 100 when it is moved over the inspection datum 15 (see arrow R in FIG. 3) and trigger the image acquisition module 12 to acquire the image of the IC 100 when it is at an appropriate location above the viewing window 17. The trigger signal may also be derived from a motion controller of the pickup head 27 (see FIG. 3). The motion controller of the pickup head 27 may have an encoder that monitors the position of the pickup head 27 and hence the location of the IC 100. It is also contemplated that the motion controller can be part of the central processing module 13 as well.

The central processing module 13 processes the digital image 60 received from the image acquisition module 12. A task of the central processing module 13 is search and locate the positions of all leads 101 in the digital image 60. It will also detect the positions of all the dynamic reference points 27, 28, 29 and 30. Using a pair of adjacent reflected sub-images, it further determines the lateral position regarding the X dimension of the IC 100. The compensation factors which involve X scale and Y scale are then computed. Using the compensation factors, the central processing module 13 computes the X, Y, Z co-ordinates of all the leads; apply the compensation factors and calculate the required parameters of the IC 100 such as coplanarity, pitch, terminal dimension and others.

One of the important functions of the control module 14 is to sense the position of the IC 100 so that it can trigger the image acquisition module 12 to acquire the image. The control module 14 further provides signals to control the movement of the light source platform 26. If required when the IC 100 is moving over the inspection datum 15, the control module will activate the light source platform to move down so as to provide a clear passage for the pickup head 27 with the IC 100. Once the IC 100 has moved over the inspection datum 15, the control module 14 will signal the light source platform 26 to move up to illuminate the leads 101. Once the IC is directly above the viewing window 17, the control module will signal the image acquisition module 12 to capture the image. Once the image or images of the IC 100 have been captured, the control module 14 will signal the light source platform to lower itself which again will provide a clear passage for the IC 100 to be moved away from the inspection datum 15.

Figure 10:
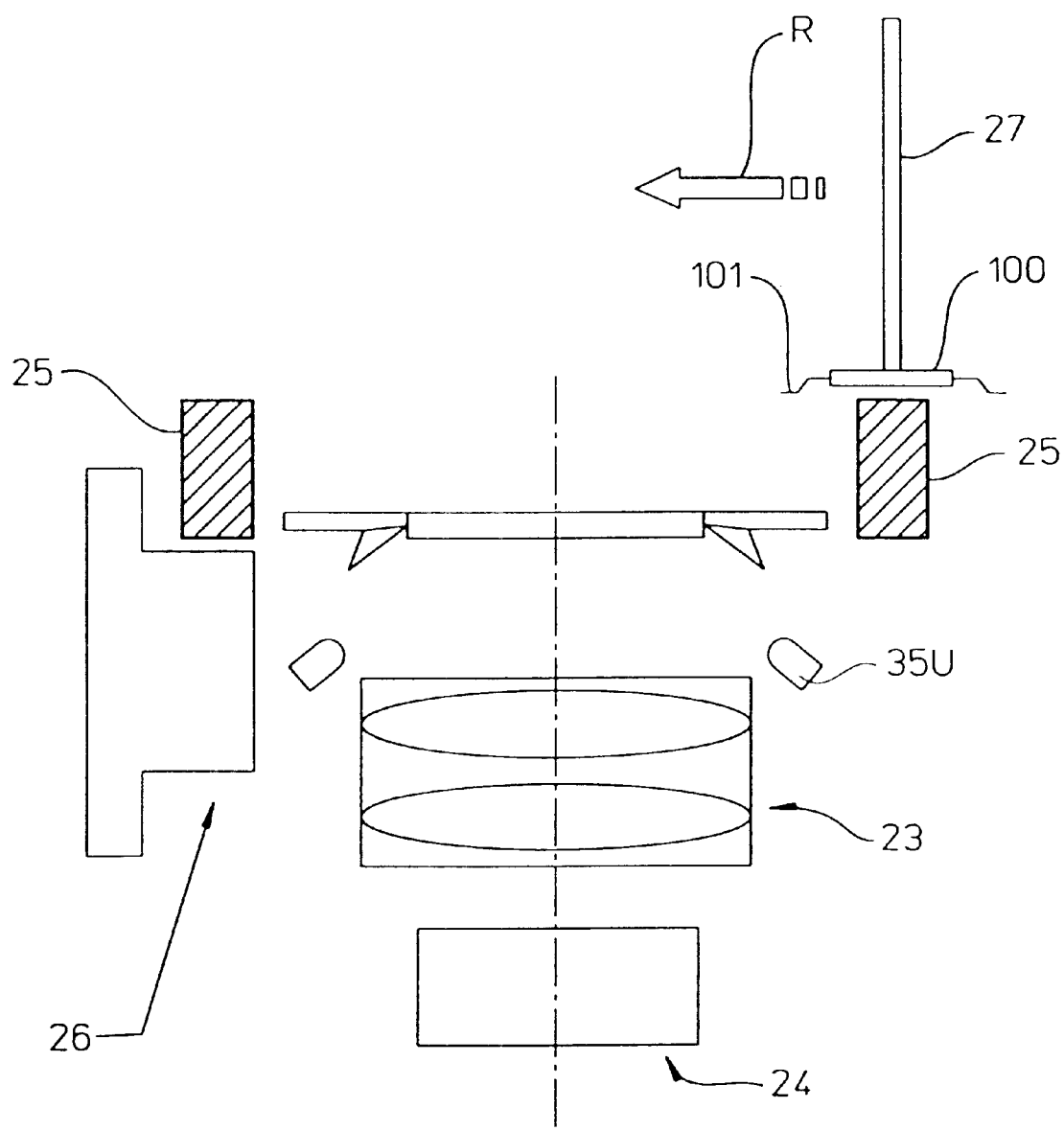
FIG. 10 is a side schematic view of another embodiment of the viewing optical module.

To provide additional imaging from another angle, in another embodiment, a light can be included to illuminate the leads from a direction at a substantial angle to the light originating from the light source 25. Preferably, to provide good reference for three-dimensional determination, the angle between light incident on or passing by closely a specific location by the two light sources is between 45 degree to 135 degree. An example would be to use a second light source to illuminate the leads from an angle about 90 degree to the light from the light source 25. FIG. 10 shows an embodiment of such an apparatus. In this embodiment, the light source 35U illuminates the IC 100 from the underside with front lighting, so that the image when seen by the video camera 24 can show the defects even on the surface of the leads or the underside surface of the IC 100. The light source 35U can have a square shape similar to the light source 25 to provide an even illumination on the leads 101 and the underside of the IC 100. Using this technique, whereby two light sources illuminate the IC leads 101 so that light from the two sources illuminate the same lead 101 at a substantial angle to one another, a defect on a lead 101 or a portion of a lead 101 that is bent and twisted in a manner which is difficult to detect using one light source can be easily detected using the other. Illuminating the underside of the object with front light, details (e.g., defects on the IC 100 package) not previously observable can be seen. This provides an additional safeguard against allowing a defective IC 100 to pass without noticing the defect. Furthermore, a second light source provides a second image, which allows three-dimensional information to be determined with only one picture of image received by the camera. In other words, in the same image received by the camera, observation is made from two different angles, thereby being able to see variations from standard in all three dimensions X, Y, and Z even without moving the object between two imaging steps. It should be noted that in this embodiment, the light source 35U is used instead of the light source 35V.

In yet another embodiment, if preferred, all three kinds of light sources 25, 35U, 35V can be used together.

Figure 11:
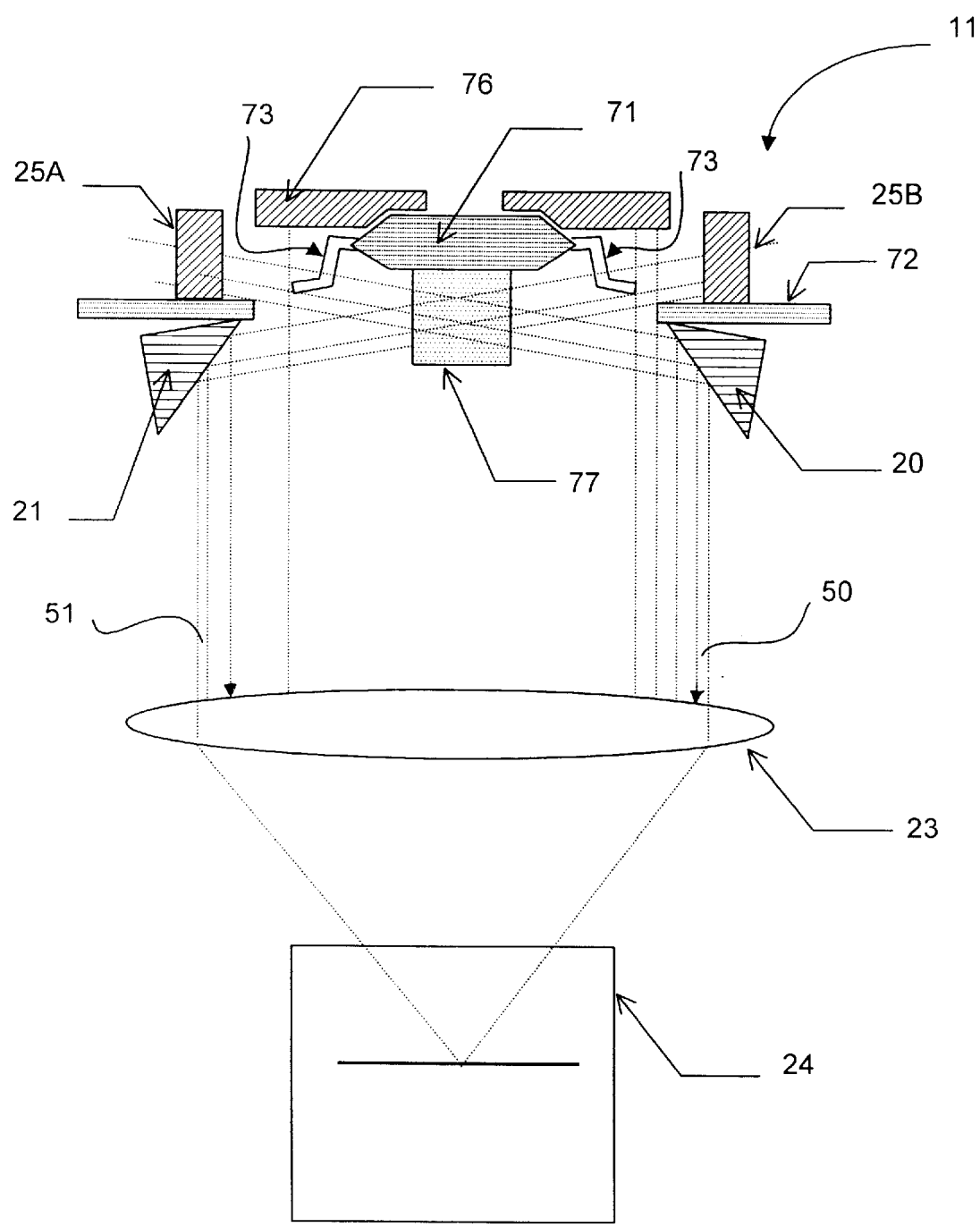
FIG. 11 is a side schematic view of a further embodiment of the viewing optical module for inspecting ICs transported on tracks.
Figure 12:
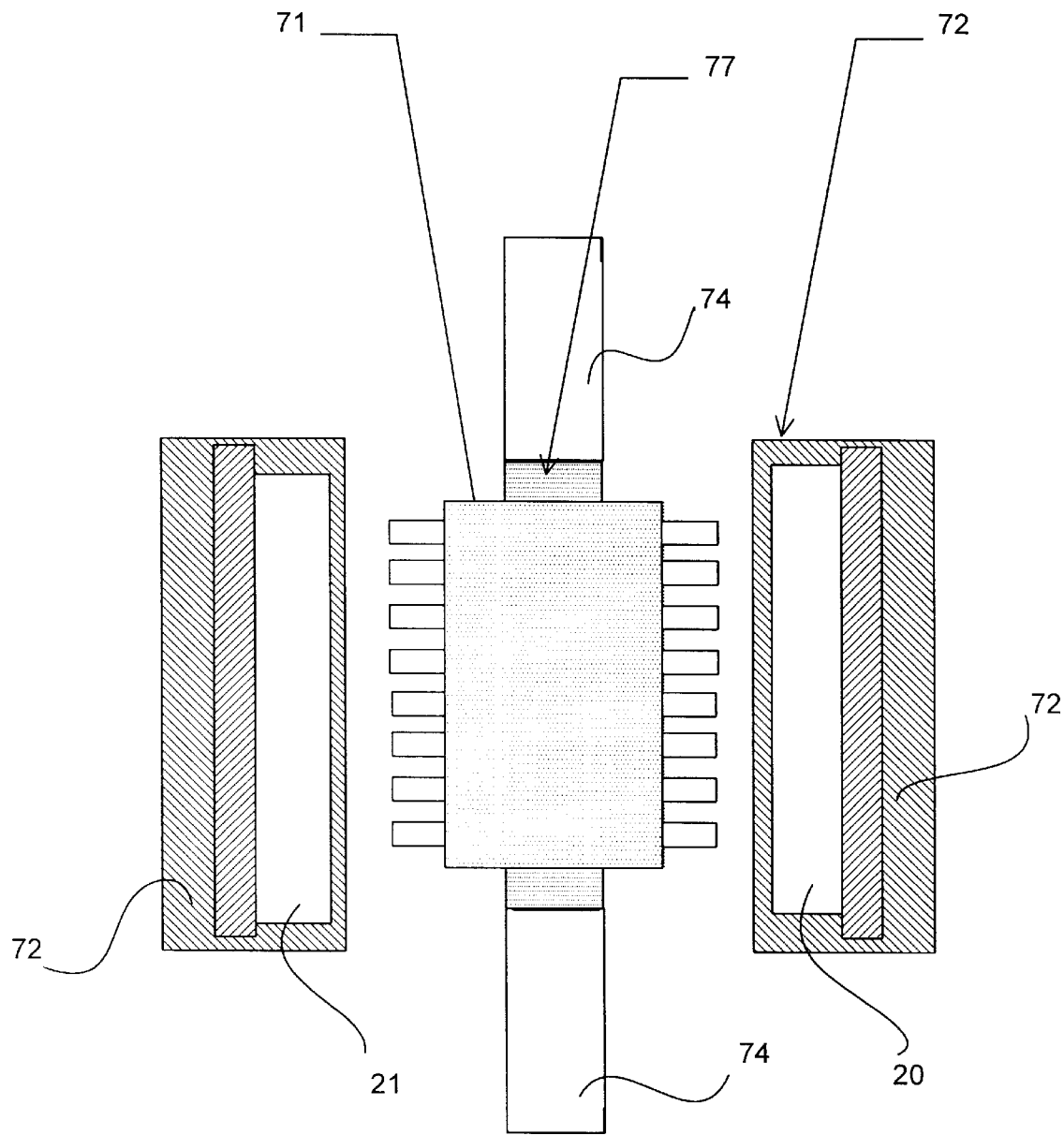
FIG. 12 is a plan schematic view of the viewing optical module in FIG. 11.

To enable the inspection system 10 to perform three-dimensional inspection of dual-sided ICs transported on tracks, in a further embodiment, a transparent guide that forms part of a track is provided. As shown in FIGS. 11 and 12, the viewing optical module 11 now includes only two opposing reflectors 20, 21 and their corresponding light source parts 25A, 25B. A dual-sided IC 71, with leads 73 only on two of its opposing sides, will traverse on the track 74 and move into a position on the transparent guide 77, as shown in FIGS. 11 and 12, for inspection. The viewing optical module 11 also includes an inspection datum 72 adapted with an opening to allow the dual-sided IC 71 to traverse on the track and onto the transparent guide 77 without obstruction, as shown in FIG. 12, and the lens 23 and the video camera 24. As before, while being positioned on the transparent guide 77, the seating plane of the dual-sided IC 71 is parallel to the inspection datum 72 and the same small spacing is maintained between them. During inspection, each of the reflectors 20, 21 views the leads 73 on the respective far side of the dual-sided IC 71, thereby forming cross-looking geometries. The reflectors 20, 21 then reflect the silhouettes of the leads 73 through the respective optical paths 50, 51 into the lens 23, and then into the video camera 24, as previously described. It should be noted that although the transparent guide 77 interposes between the light source parts 25A, 25B and the reflectors 20, 21, the angle of the light in the optical paths 50, 51 incident at the reflectors 20, 21 is not affected. This is because the transparent guide 77 has a pair of planar and parallel opposing surfaces, and therefore light propagating through the transparent guide 77 and leaving one surface, or outbound light, will remain in parallel with the light entering the other surface, or inbound light. Preferably, the transparent guide 77 is made of hard glass, fused silica, Sapphire or plastic that are grounded and polished using known optical components processing methods. Furthermore, these surfaces are coated with known anti-reflection substances to prevent the straying of the light, thereby reducing light loss and maintaining the integrity of the image of the silhouettes at the reflectors 20, 21.

In addition to the transparent guide 77, the viewing optical module 11 is also provided with a top guide 76. The top guide 76, as shown in FIG. 11, is profiled such that a portion of it follows the upper surfaces of the dual-sided IC 71 so that it can co-operate with the transparent guide 77 to hold the dual-sided IC 71 in place for inspection. The top guide 76 also co-operates with the transparent guide 77 to provide a channel for the dual-sided IC 71 to traverse. In addition, the top guide 76 serves as a backlight means for providing a silhouette image of the dual-sided IC 71 package to the video camera 24 through the lens 23, as described previously. By making the top guide 76 from diffused material, for example white Deldrin, and providing it with internally conducted light, the backlight means can be achieved.

Figure 13A:
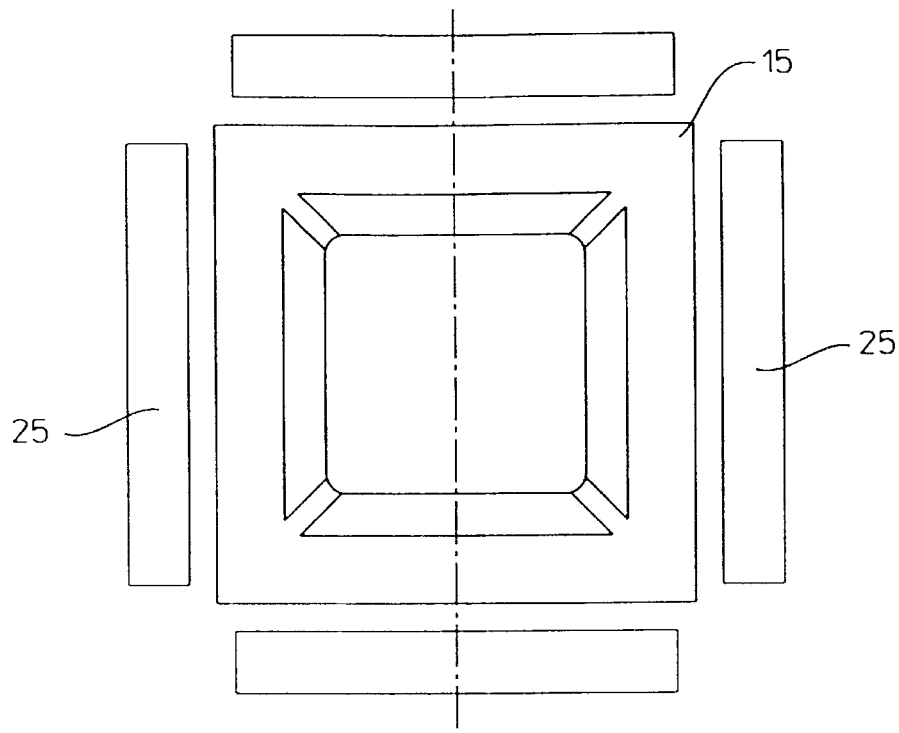
FIGS. 13a and 13b are a plan schematic view and a cross-sectional schematic elevation respectively of a variation of the embodiments of the viewing optical module.
Figure 13B:
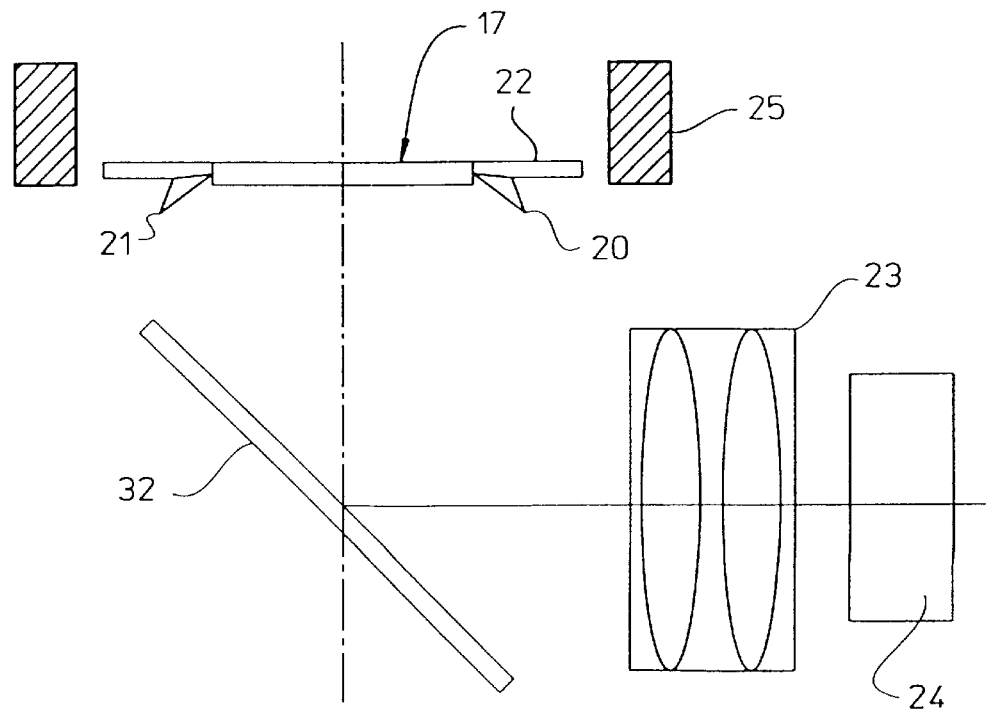

There are many other variations to the specific embodiments of the present invention. For example, as illustrated in FIGS. 13a and 13b, it is possible to include a mirror 32 to redirect the light by 90 degree so that the lens 23 and the video cameras 24 can be aligned horizontally rather than vertically. In this case, in the present disclosure, the optical axis of the video camera 24 is still considered to pass through the plane of the IC 100 in the window. This example illustrates the possibility of changing the physical layout of the present invention.

The invention has been designed with consideration of, but not exclusively, for the inspection of integrated circuit leads and embodiments of the invention herein have been described in that context. However, it is to be appreciated that the invention has broader applications and is not limited to that particular use. It will be appreciated that various modifications and improvements as well as additions can be made to the parts hereinafter before described without departing from the spirit or ambit of the present invention.

We claim:

1. An apparatus for inspecting an object having a plane, comprising:
   a camera for sensing an image of the object, the camera having an optical axis passing through the object substantially normal to the plane of the object;
   an oblique light source for radiating light on the object obliquely to the plane of the object to create an image of a portion of the object, the oblique light source having a portion positioned on one side of the optical axis;
   a reflector positioned on the opposite side of the optical axis relative to the portion of the oblique light source for reflecting light that crosses the optical axis from the oblique light source to the camera, such that the image of the object portion is reflected to the camera; and
   a guide for disposing the object in the apparatus in relation to the oblique light source and the reflector, wherein the guide is interposed between the portion of the oblique light source and the reflector and made of light transmissible material.

2. The apparatus as in claim 1, further comprising a planar datum having an opening through which the light from the oblique light source passes for imaging the shape of the portion of the object on the camera, and an edge that interposes between the oblique light source and the reflector so that an image of the edge is reflected to the camera to provide a reference for inspecting the object.

3. The apparatus as in claim 2, wherein the guide further includes a pair of substantially planar and parallel opposing surfaces where one of the pair of opposing surfaces receives the radiated light and the other transmits the radiated light which propagated through the guide.

4. The apparatus as in claim 2, wherein the guide is made of sapphire.

5. The apparatus as in claim 2, wherein the guide is coated with anti-reflection substances.

6. The apparatus as in claim 2, wherein the guide further includes a surface that seats the object for disposing the object in the apparatus.

7. The apparatus as in claim 2, further comprising a top guide that co-operates with the light transmissible guide for disposing the object in the apparatus.

8. The apparatus as in claim 7, wherein the top guide is profiled to follow the upper surface of the object for co-operating with the light transmissible guide to dispose the object in the apparatus.

9. The apparatus as in claim 7, wherein the top guide is made of a diffused material so that it forms lighting means when it is provided with internally conducted light.

10. An apparatus for disposing an object having a plane in a cross imaging system having a camera, an oblique light source, and a cross-looking reflector, wherein the object is transported by a track, the apparatus comprising:
    a first guide made of light transmissible material, wherein the first guide forms part of the track that transports the object, receives the light radiated from the oblique light source, and allows such light to propagate through it; and
    a second guide that co-operates with the first guide to dispose the object in the cross imaging system in relation to the oblique light source and the cross-looking reflector.

11. The apparatus as in claim 10, wherein the first guide further includes a pair of substantially planar and parallel opposing surfaces, one of the pair of opposing surfaces receiving the radiated light and the other transmits the internally propagated radiated light.

12. The apparatus as in claim 10, wherein the first guide is made of sapphire.

13. The apparatus as in claim 10, wherein the first guide is coated with anti-reflection substances.

14. The apparatus as in claim 10, wherein the first guide further includes a surface that seats the object for disposing the object in the apparatus.

15. The apparatus as in claim 10, wherein the second guide is profiled to follow the upper surface of the object for co-operating with the first guide to dispose the object in the cross-imaging system.

16. The apparatus as in claim 15, wherein the second guide is made of a diffused material so that it forms lighting means when it is provided with internally conducted light.

17. A method of inspecting the quality of an object having a plane using a camera, a reflector, a light source and a light transmissible holder, comprising the steps of:
    disposing the object relative to the reflector and the light source using the light transmissible holder;
    interposing the light transmissible holder between the light source and the reflector;
    propagating the light from the light source through the light transmissible holder, positioning the camera having an optical axis to view the object for sensing an image such that the optical axis is substantially normal to the plane of the object; and directing light from the light source past a portion of the object obliquely relative to the plane of the object to impinge on the reflector that is positioned on the opposite side of the optical axis relative to the light source such that the light is reflected from the reflector to image the shape of the portion of the object on the camera, the shape indicating the quality of the object.

* * * * *